(12) United States Patent
Skiba

(10) Patent No.: US 6,689,153 B1
(45) Date of Patent: Feb. 10, 2004

(54) METHODS AND APPARATUS FOR A COATED ANCHORING DEVICE AND/OR SUTURE

(75) Inventor: Jeffry B. Skiba, Santa Rosa, CA (US)

(73) Assignee: Orthopaedic Biosystems Ltd, Inc., Memphis, TN (US)

(*) Notice: Subject to any disclaimer, the term of this patent is extended or adjusted under 35 U.S.C. 154(b) by 0 days.

(21) Appl. No.: 09/548,975

(22) Filed: Apr. 14, 2000

Related U.S. Application Data
(60) Provisional application No. 60/129,675, filed on Apr. 16, 1999.

(51) Int. Cl.$^7$ ................................................ A61B 17/04
(52) U.S. Cl. ..................... 606/232; 606/230; 606/231
(58) Field of Search .......................................... 606/232

(56) References Cited

U.S. PATENT DOCUMENTS

| | | |
|---|---|---|
| 1,105,105 A | 7/1914 | Sherman |
| 2,100,570 A | 11/1937 | Rohmer Saleh |
| 2,143,086 A | 1/1939 | Pleister |
| 2,242,003 A | 5/1941 | Lorenzo |
| 2,381,050 A | 8/1945 | Hardinge |
| 2,397,545 A | 4/1946 | Hardinge |
| 2,414,882 A | 1/1947 | Longfellow |
| 2,570,465 A | 10/1951 | Lundholm |

(List continued on next page.)

FOREIGN PATENT DOCUMENTS

| | | |
|---|---|---|
| EP | 0 232 049 A1 | 8/1987 |
| EP | 0 241 240 A2 | 10/1987 |
| EP | 0 260 970 A2 | 3/1988 |
| EP | 0 270 704 A1 | 6/1988 |
| EP | 0 340 159 A1 | 11/1989 |
| EP | 0 374 088 A1 | 6/1990 |
| EP | 0 409 364 A2 | 1/1991 |
| EP | 0 451 932 A | 10/1991 |
| EP | 0 464 480 | 8/1992 |
| EP | 0 502 509 A1 | 9/1992 |
| EP | 0 528 573 A1 | 2/1993 |
| EP | 0 574 707 | 12/1993 |
| EP | 0 615 732 A1 | 7/1994 |
| EP | 0 674 880 A1 | 10/1995 |
| FR | 2 622 430 | 5/1989 |
| WO | WO 85/03857 | 9/1985 |
| WO | WO 86/03666 | 7/1986 |
| WO | WO 87/01270 | 3/1987 |
| WO | WO 88/09157 | 12/1988 |
| WO | WO 89/09030 | 10/1989 |
| WO | WO 89/10096 | 11/1989 |
| WO | WO 92/04874 | 4/1992 |
| WO | WO 95/15726 | 6/1995 |
| WO | WO 95/25469 | 9/1995 |
| WO | WO 95/27449 | 10/1995 |
| WO | WO 95/29637 | 11/1995 |
| WO | WO 97/30639 | 8/1997 |

OTHER PUBLICATIONS

"Anterior Cruciate Ligament Allograft Transplatation Long–term Function, Histology, Revascularization, and Operative Technique," Pantelis K. Nikolaou, M.D., Anthony V. Seaber, Richard R. Glisson, Beth M. Ribbeck, MS, and Frank H. Bassett III, M.D., *American Journal of Sports Medicine*, 14(5):348–360 (1986).

(List continued on next page.)

*Primary Examiner*—Gary Jackson
(74) *Attorney, Agent, or Firm*—Fish & Richardson P.C.

(57) ABSTRACT

A coated/impregnated anchoring device and/or suture to prevent infection, deliver site specific drugs, and deliver human growth factors to the surgical site. The coatings can include anti-microbial agents to prevent or fight infection en route to and at the surgical site. The coatings can also include site specific drugs and/or human growth factors to fight infection, anesthetize tissue and/or bone en route and at the site, promote tissue regeneration, promote bone regeneration, and/or other desired medical processes.

30 Claims, 4 Drawing Sheets

U.S. PATENT DOCUMENTS

| | | |
|---|---|---|
| 2,685,877 A | 8/1954 | Dobelle |
| 3,003,155 A | 10/1961 | Mielzynski et al. |
| 3,123,077 A | 3/1964 | Alcamo |
| 3,273,442 A | 9/1966 | Launay |
| 3,289,290 A | 12/1966 | Sandor |
| 3,312,139 A | 4/1967 | Di Cristina |
| 3,316,796 A | 5/1967 | Young |
| 3,405,595 A | 10/1968 | Peterson |
| 3,463,209 A | 8/1969 | Podolsky |
| 3,499,222 A | 3/1970 | Linkow et al. |
| 3,566,739 A | 3/1971 | Lebar |
| 3,708,883 A | 1/1973 | Flander |
| 3,716,058 A | 2/1973 | Tanner, Jr. |
| 3,888,144 A | 6/1975 | Parsons |
| 3,910,281 A | 10/1975 | Kletschka et al. |
| 3,976,079 A | 8/1976 | Samuels et al. |
| 3,987,797 A | 10/1976 | Stephenson |
| 4,011,602 A | 3/1977 | Rybicki et al. |
| 4,013,071 A | 3/1977 | Rosenberg |
| 4,175,555 A | 11/1979 | Herbert |
| 4,275,717 A | 6/1981 | Bolesky |
| 4,409,974 A | 10/1983 | Freedland |
| 4,463,753 A | 8/1984 | Gustilo |
| 4,469,101 A | 9/1984 | Coleman et al. |
| 4,476,590 A | 10/1984 | Scales et al. |
| 4,484,570 A | 11/1984 | Sutter et al. |
| 4,493,323 A | 1/1985 | Albright et al. |
| 4,532,926 A | 8/1985 | O'Holla |
| 4,537,185 A | 8/1985 | Stednitz |
| 4,548,202 A | 10/1985 | Duncan |
| 4,573,844 A | 3/1986 | Smith |
| 4,632,100 A | 12/1986 | Somers et al. |
| 4,636,121 A | 1/1987 | Miller |
| 4,662,886 A | 5/1987 | Moorse et al. |
| 4,708,132 A | 11/1987 | Silvestrini |
| 4,711,232 A | 12/1987 | Fischer et al. |
| 4,711,234 A | 12/1987 | Vives et al. |
| 4,716,893 A | 1/1988 | Fischer et al. |
| 4,744,793 A | 5/1988 | Parr et al. |
| 4,759,765 A | 7/1988 | Van Kampen |
| 4,772,286 A | 9/1988 | Goble et al. |
| 4,776,328 A | 10/1988 | Frey et al. |
| 4,776,329 A | 10/1988 | Treharne |
| 4,776,330 A | 10/1988 | Chapman et al. |
| 4,851,005 A | 7/1989 | Hunt et al. |
| 4,870,957 A | 10/1989 | Goble et al. |
| 4,871,289 A | 10/1989 | Choiniere |
| 4,873,976 A | 10/1989 | Schreiber |
| 4,884,572 A | 12/1989 | Bays et al. |
| 4,895,148 A | 1/1990 | Bays et al. |
| 4,898,156 A | 2/1990 | Gatturna et al. |
| 4,899,743 A | 2/1990 | Nicholson et al. |
| 4,917,554 A | 4/1990 | Bronn |
| 4,924,865 A | 5/1990 | Bays et al. |
| 4,927,421 A | 5/1990 | Goble et al. |
| 4,940,467 A | 7/1990 | Tronzo |
| 4,946,468 A | 8/1990 | Li |
| 4,950,270 A | 8/1990 | Bowman et al. |
| 4,968,315 A | 11/1990 | Gatturna |
| 4,976,715 A | 12/1990 | Bays et al. |
| 4,988,351 A | 1/1991 | Paulos et al. |
| 4,997,433 A | 3/1991 | Goble et al. |
| 5,002,550 A | 3/1991 | Li |
| 5,013,316 A | 5/1991 | Goble et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,061,181 A | 10/1991 | Niznick |
| 5,067,956 A | 11/1991 | Buford, III et al. |
| 5,084,050 A | 1/1992 | Draenert |
| 5,098,434 A | 3/1992 | Serbousek |
| 5,100,417 A | 3/1992 | Cerier et al. |
| 5,102,421 A | 4/1992 | Anspach, Jr. |
| 5,129,906 A | 7/1992 | Ross et al. |
| 5,141,520 A | 8/1992 | Goble et al. |
| 5,152,765 A | 10/1992 | Ross et al. |
| 5,156,616 A | 10/1992 | Meadows et al. |
| D331,626 S | 12/1992 | Hayhurst et al. |
| 5,176,682 A | 1/1993 | Chow |
| 5,192,303 A | 3/1993 | Gatturna et al. |
| 5,203,787 A | 4/1993 | Noblitt et al. |
| 5,207,679 A | 5/1993 | Li |
| 5,209,753 A | 5/1993 | Biedermann et al. |
| 5,211,647 E | 5/1993 | Schmieding |
| RE34,293 E | 6/1993 | Goble et al. |
| 5,217,486 A | 6/1993 | Rice et al. |
| 5,224,946 A | 7/1993 | Hayhurst et al. |
| 5,234,430 A | 8/1993 | Huebner |
| 5,246,441 A | 9/1993 | Ross et al. |
| 5,258,016 A | 11/1993 | DiPoto et al. |
| 5,268,001 A | 12/1993 | Nicholson et al. |
| 5,282,832 A | 2/1994 | Toso et al. |
| 5,306,290 A | 4/1994 | Martins et al. |
| 5,312,438 A | 5/1994 | Johnson |
| 5,324,308 A | 6/1994 | Pierce |
| 5,326,205 A | 7/1994 | Anspach, Jr. et al. |
| 5,336,225 A | 8/1994 | Zang |
| 5,336,240 A | 8/1994 | Metzler et al. |
| 5,354,298 A | 10/1994 | Lee et al. |
| 5,354,299 A | 10/1994 | Coleman |
| 5,356,413 A | 10/1994 | Martins et al. |
| 5,358,511 A | 10/1994 | Gatturna et al. |
| 5,370,662 A | 12/1994 | Stone et al. |
| 5,372,599 A | 12/1994 | Martins |
| 5,372,604 A | 12/1994 | Trott |
| 5,383,878 A | 1/1995 | Roger et al. |
| RE34,871 E | 3/1995 | McGuire et al. |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,423,819 A | 6/1995 | Small et al. |
| 5,425,733 A | 6/1995 | Schmieding |
| 5,425,767 A | 6/1995 | Steininger |
| 5,441,502 A | 8/1995 | Bartlett |
| 5,443,482 A | 8/1995 | Stone et al. |
| 5,443,509 A | 8/1995 | Boucher et al. |
| 5,454,811 A | 10/1995 | Huebner |
| 5,456,685 A | 10/1995 | Huebner |
| 5,458,601 A | 10/1995 | Young, Jr. et al. |
| 5,464,425 A | 11/1995 | Skiba |
| 5,464,427 A | 11/1995 | Curtis et al. |
| 5,466,243 A | 11/1995 | Schmieding et al. |
| 5,470,334 A | 11/1995 | Ross et al. |
| 5,472,452 A | 12/1995 | Trott |
| 5,480,403 A | 1/1996 | Lee et al. |
| 5,486,197 A | 1/1996 | Le et al. |
| 5,489,210 A | 2/1996 | Hanosh |
| 5,496,326 A | 3/1996 | Johnson |
| 5,500,001 A | 3/1996 | Trott |
| 5,501,683 A | 3/1996 | Trott |
| 5,501,695 A | 3/1996 | Anspach, Jr. et al. |
| 5,501,696 A | 3/1996 | Trott |
| 5,505,735 A | 4/1996 | Li |
| 5,520,696 A | 5/1996 | Wenstrom, Jr. |
| 5,522,843 A | 6/1996 | Zang |
| 5,522,845 A | 6/1996 | Wenstrom, Jr. |
| 5,545,178 A | 8/1996 | Kensey et al. |
| 5,545,180 A | 8/1996 | Le et al. |
| 5,554,171 A | 9/1996 | Gatturna et al. |
| 5,571,104 A | 11/1996 | Li |

| | | |
|---|---|---|
| 5,571,139 A | 11/1996 | Jenkins, Jr. |
| 5,573,548 A | 11/1996 | Nazre et al. |
| 5,578,044 A | 11/1996 | Gordon et al. |
| 5,578,057 A | 11/1996 | Wenstrom, Jr. |
| 5,584,835 A | 12/1996 | Greenfield |
| 5,584,836 A | 12/1996 | Ballintyn et al. |
| 5,591,207 A | 1/1997 | Coleman |
| 5,601,557 A | 2/1997 | Hayhurst |
| 5,607,432 A | 3/1997 | Fucci |
| 5,626,613 A | 5/1997 | Schmieding |
| 5,630,824 A | 5/1997 | Hart |
| 5,632,748 A | 5/1997 | Beck, Jr. et al. |
| 5,643,320 A | 7/1997 | Lower et al. |
| 5,643,321 A | 7/1997 | McDevitt |
| 5,645,589 A | 7/1997 | Li |
| 5,647,874 A | 7/1997 | Hayhurst |
| 5,649,963 A | 7/1997 | McDevitt |
| 5,662,654 A | 9/1997 | Thompson |
| 5,662,658 A | 9/1997 | Wenstrom, Jr. |
| 5,662,683 A | 9/1997 | Kay |
| 5,669,935 A | 9/1997 | Rosenman et al. |
| 5,683,401 A | 11/1997 | Schmieding et al. |
| 5,683,418 A | 11/1997 | Luscombe et al. |
| 5,690,649 A | 11/1997 | Li |
| 5,690,676 A | 11/1997 | DiPoto et al. |
| 5,690,677 A | 11/1997 | Schmieding et al. |
| 5,697,950 A | 12/1997 | Fucci et al. |
| 5,707,395 A | 1/1998 | Li |
| 5,715,942 A | 2/1998 | Li et al. |
| 5,720,766 A | 2/1998 | Zang et al. |
| 5,725,529 A | 3/1998 | Nicholson et al. |
| 5,725,557 A | 3/1998 | Gatturna et al. |
| 5,728,116 A | 3/1998 | Rosenman |
| 5,741,300 A | 4/1998 | Li |
| 5,743,914 A | 4/1998 | Skiba |
| 5,782,864 A | 7/1998 | Lizardi |
| 5,782,866 A | 7/1998 | Wenstrom, Jr. |
| 5,797,963 A | 8/1998 | McDevitt |
| 5,800,447 A | 9/1998 | Wenstrom, Jr. |
| 5,814,071 A | 9/1998 | McDevitt et al. |
| 5,827,291 A | 10/1998 | Fucci et al. |
| 5,851,219 A | 12/1998 | Goble et al. |
| 5,860,978 A | 1/1999 | McDevitt et al. |
| 5,871,490 A | 2/1999 | Schulze et al. |
| 5,885,294 A | 3/1999 | Pedlick et al. |
| 5,893,856 A | 4/1999 | Jacob et al. |
| 5,895,396 A | 4/1999 | Day et al. |
| 5,895,425 A | 4/1999 | Grafton et al. |
| 5,899,938 A | 5/1999 | Sklar et al. |
| 5,904,696 A | 5/1999 | Rosenman |
| 5,904,704 A | 5/1999 | Goble et al. |
| 5,911,721 A | 6/1999 | Nicholson et al. |
| RE36,289 E | 8/1999 | Le et al. |
| 5,931,840 A | 8/1999 | Goble et al. |
| 5,935,134 A | 8/1999 | Pedlick et al. |
| 5,951,997 A * | 9/1999 | Bezwada et al. ........... 424/426 |
| 5,961,538 A | 10/1999 | Pedlick et al. |
| 5,964,783 A | 10/1999 | Grafton et al. |
| 5,968,044 A | 10/1999 | Nicholson et al. |
| 5,971,987 A | 10/1999 | Huxel et al. |
| 5,984,927 A | 11/1999 | Wenstrom, Jr. et al. |
| 5,993,477 A | 11/1999 | Vaitekunas et al. |
| 6,007,566 A | 12/1999 | Wenstrom, Jr. |
| 6,019,768 A | 2/2000 | Wenstrom, Jr. et al. |
| 6,027,523 A | 2/2000 | Schmieding |
| 6,036,701 A | 3/2000 | Rosenman |
| 6,045,573 A | 4/2000 | Wenstrom, Jr. et al. |
| 6,056,778 A | 5/2000 | Grafton et al. |
| 6,074,395 A | 6/2000 | Trott et al. |
| 6,080,184 A | 6/2000 | Peters et al. |
| 6,086,591 A | 7/2000 | Bojarski |
| 6,096,060 A | 8/2000 | Fitts et al. |
| 6,099,568 A | 8/2000 | Simonian et al. |
| 6,117,162 A | 9/2000 | Schmieding et al. |
| 6,139,565 A | 10/2000 | Stone et al. |
| 6,146,387 A | 11/2000 | Trott et al. |
| 6,146,406 A | 11/2000 | Shluzas et al. |
| 6,179,840 B1 | 1/2001 | Bowman |
| 6,214,031 B1 | 4/2001 | Schmieding et al. |

OTHER PUBLICATIONS

"Vascularized Patellar Tendon Graft with Rigid Internal Fixation for Anterior Cruciate Ligament Insufficiency," Kenneth L. Lambert, MD, Clinical Orthopedics and Related Research, 172, Jan.–Feb. (1983).

Advertisement, Innovasive Devices Brochures, Feb. 1995.

Rushton, D.N., Brindley, G.S., Polkey, C.E. and Browning, G.V., "Implant Infections and Antibiotic–Impregnated Silicone Rubber Coating," Journal of Neurology, Neurosurgery, and Psychiatry, (1989), pp. 223–229.

Fish, Douglas N., Hoffman, Heather M. and Danziger, Larry H., "Antibiotic–Impregnated Cement Use in U.S. Hospitals," American Journal Hospital Pharmacists, vol. 49, (Oct. 1992), pp. 2469–2474.

Henry, M.D., Stephen L., Ostermann, M.D., Peter A.W. and Seligson, M.D., David, "The Antibiotic Bead Pouch Technique: The Management of Severe Compound Fractures," Clinical Orthopaedics and Related Research, No. 295, (1993), pp. 54–62.

Gref, Ruxandra, Minamitake, Yoshiharu, Peracchia, Maria Teresa, Trubetskoy, Vladimir, Torchilin, Vladimir and Langer, Robert, "Biodegradable Long–Circulating Polymeric Nanospheres," Science, vol. 263 (Mar. 18, 1994), pp. 1600–1603.

Barber, M.D., F. Alan, Herber, Ph.D., Morley A. and Click, P.A.–C., James N., "The Ultimate Strength of Suture Anchors," Arthroscopy: The Journal of Arthoroscopic and Related Surgery, vol. 11, No. 1 (Feb. 1995), pp. 21–28.

Product List For American Cyanamid Co., pp. ii–v—"Absorbable Sutures," American Cyanamid Co., p. ii—"Nonabsorbable Sutures," American Cyanamid Co., pp. iii–v.

Ticker, M.D., Jonathan B., Lippe, M.D., Robert J., Barkin, M.D., Douglas E. and Carroll, M.D., Michael P., "Infected Suture Anchors in the Shoulder," Arthroscopy: The Journal of Arthoroscopic and Related Surgery, vol. 12, No. 5 (Oct. 1996), pp. 613–615.

Radomsky, M., Merck, A., Gonslaves, M., Anudokem, G. and Poser J., "Basic Fibroblast Growth Factor in a Hyaluronic Acid Gel Stimulates Intramebranous Bone Formation," 43rd Annual Meeting, Orthopaedic Research Society, (Feb. 1997, S.F., CA), p. 510.

Wakitani, S., Imoto, K., Murata, N., Oonishi, H., Kimura, T., Tomita, T., Ochi, T., Matsumoto, K. and Nakamura, T., "The Effect of Hepatocyte Growth Factor on Repair of Rabbit Articular Cartilage Defect," 43rd Annual Meeting, Orthopaedic Research Society, (Feb. 1997, S.F., CA), p. 512.

Sperling, J.W., Fitzsimmons, J.S. and O'Driscoll, S.W., "Growth Hormone Enhancement of Chondrogenesis in Periosteal Explants," 43rd Annual Meeting, Orthopaedic Research Society, (Feb. 1997, S.F., CA), p. 513.

Reynolds, S.D., Reyolds, P.R., Moylan, P.E. and Anderson, H.C., "Identification of Bone Morphogenetic Protein–1 (BMP–1) in Osteoinductive SAOS–2 Cell Products and Induced Heteroptopic Bone," 43rd Annual Meeting, Orthopaedic Research Society, (Feb. 1997, S.F., CA), p. 525.

Brager, M.A., Patterson, M.J., Gibson, J.S., Connolly, J.F. and Nevo, Z., "The Effect of Osteogenic Growth Peptide Injections on Fracture Healing in Rats," 43rd Annual Meeting, Orthopaedic Research Society, (Feb. 1997, S.F., CA), p. 527.

Lind, M., Overgaard, S., Glenup, M., Bunger, C., and Soballe, K., "Transforming Growth Factor–B1 Accelerates Bone Cell Repair Activity in a Gap Around Ceramic Coated Implants in Dogs," 43rd Annual Meeting, Orthopaedic Research Society, (Feb. 1997, S.F., CA), p. 528.

Kim, H.D., Smith, J.G. and Valentini, R.F., "Bone Morphogenetic Protein–2 Induction of Pluripotent C3H10T1/2 Cells in Porous PLLA Scaffolds," 43rd Annual Meeting, Orthopaedic Research Society, (Feb. 1997, S.F., CA), p. 546.

Santos, E.M., Ducheyne, P., Radin, S. and Shapiro, I.M., "The Effect of Bioactive Xerogel Glass With and Without Bone Morphogenetic Protien on Stromal Marrow Cell Function," 43rd Annual Meeting, Orthopaedic Research Society, (Feb. 1997, S.F., CA), p. 547.

Hanlon, J., Yaeger, P., McPherson, J., Tubo, R. and Binette, F., "Redifferentiation of Passaged Human Articular Chondrocytes in Type–I Collagen Sponges is Enhanced with Transforming Growth Factor–B Supplementation," 43rd Annual Meeting, Orthopaedic Research Society, (Feb. 1997, S.F., CA), p. 551.

Barber, M.D., F. Alan, Cherf, M.D., MPH, John M. and McCarty, CSCS, AT, C, Timothy M., "Suture Anchors Product Information Guide," Orthopedic Special Edition, (Winter/Spring 1997), pp. 1–8.

Gupta, Bhupender S., "Medical Textile Structures: An Overview," Medical Plastics and Biomaterials Magazine (MPB Archive), (Jan. 1998) also available on http://www.devicelink.com/mpb/archive/98/01/001.html.

Tunney, Michael M., Ramage, Gordon, Patrick, Sheila, Nixon, James R., Murphy, Philip G. and Gorman, Sean P., "Antimicrobial Susceptibility of Bacteria Isolated From Orthopedic Implants Following Revision Hip Surgery," Antimicrobial Agents Chemotherapy, vol. 42, No. 11, (Nov. 1998), pp. 3002–3005 also available on http://aac.asm.org/cgi/content/full/42/11/3002.

Murata, M., Huang, B.Z., Shibata, T., Imai, S., Nagai, N. and Arisue, M., "Bone Augmentation by Recombinant Human BMP–2 and Collagen on Adult Rat Parietal Bone," International Journal of Oral and–Maxillofacial Surgery, vol. 28, No. 3 (Jun. 1999), pp. 232–237.

Carnes, Jr., D.L., De La Fontaine, J., Cochran, D.L., Mellonig, J.T., Keogh, B., Harris, S.E., Chosh–Choudhury, N., Dean, D.D., Boyan, B.D. and Schwartz, Z., "Evaluation of 2 Novel Approaches For Assessing the Ability of Demineralized Freeze–Dired Boe Allograft to Induce New Bone Formation," Journal of Periodontology, vol. 70, No. 4, (Apr. 1999), pp. 353–363.

Kleef, J., Maruyama, H. Ishiwata, T., Sawhney, H., Friess, H., Buchler, M.W. and Korc, M., "Bone Morphogenetic Protein 2 Exerts Diverse Effects on Cell Growth in Vitro and is Expressed in Human Pancreatic Cancer in Vivo," Gastroenterology, vol. 116, No. 5, (May 1999), pp. 1202–1206.

Ono, I., Tateshita, T., Takita, H. and Kuboki, Y., "Promotion of the Osteogenetic Activity of Recombinant Human Bone Morphogenetic Protein by Basic Fibroblast Growth Factor," Journal of Carniofacial Surgery, vol. 7, No. 6 (Nov. 1996), pp. 418–425.

Scheufler, C., Sebald, W. and Hulsemeyer, "Crystal Structure o f Human Bone Morphogenetic Protien–2 at 2.7 A Resolution," Journal of Molecular Biology, vol. 287, No. 1, (Mar. 1999), pp. 103–115.

Schwartz, Z., Somers, A., Mellonig, J.T., Carnes, Jr., D.L., Wozney, J.M., Dean, D.D., Cochran, D.L. and Boyan, B.D., "Addition of Human Recombinant Bone Morphogenetic Protein–2 to Inactive Commercial Human Demineralized Freeze–Dried Bone Allograft Makes an Effective Composite Bone Inductive Implant Materials," Journal of Periodontology, vol. 69, No. 12, (Dec. 1998), pp. 1337–1345.

DeGroot, J., "Carriers That Concentrate Native Bone Morphogenetic Protien in Vivo," Tissue Engineering, vol. 4, No. 4, (Winter 1998), pp. 337–341.

Whang, K., Tsai, D.C., Nam, E.K., Aitken, M., Sprague, S.M., Patel, P.K. and Healy, K.E., "Ectopic Bone Formation Via rhBMP–2 Delivery From Porous Bioabsorbable Polymer Scaffolds," Journal of Biomedical Materials Research, vol. 42, No. 4, (Dec. 1998), pp. 491–499.

Lind, M., "Growth Factor Stimulation of Bone Healing. Effects on Osteoblasts, Osteomies, and Implants Fixation," Acta Orthopaedica Scandinavica Supplementum, vol. 283, (Oct. 1998), pp. 2–37.

Illi, O.E., and Feldmann, C.P., "Stimulation of Fracture Healing by Local Application of Humoral Factors Integrated in Biodegradable Implants," European Journal of Pediatric Surgery, vol. 8, No. 4 (Aug. 1998), pp. 251–255.

Si, S., Jin, Y. and Yang, L., "Induction of New Bone by Ceramic Bovine Bone With Recombinant Human Bone Morphogenetic Protein 2 and Transforming Growth Factor Beta," International Journal of Oral and Maxillofacial Surgery, vol. 27, No. 4 (Aug. 1998), pp. 310–314.

Yamamoto, M., Tabata, Y. and Ikada, Y., "Ectopic Bone Formation Induced by Biodegradable Hydrogels Incorporating Bone Morphogenetic Protein," Journal of Biomaterials Science, Polymer Edition, vol. 9, No. 5, (1998), pp. 439–458.

Soda, H., Raymond, E., Sharma, S., Lawrence, R., Cerna, C., Gomez, L., Timony, G.A., Von Hoff, D.D., and Izbicka, E., "Antiproliferation Effects of Recombinant Human Bone Morphogenetic Protein–2 on Human Tumor Colony–Forming Units," Anti–Cancer Drugs, vol. 9, No. 4, (Apr. 1998), pp. 327–331.

Schwartz, Z., Somers, A., Mellonig, J.T., Carnes, Jr., D.L., Dean, D.D., Cochran, D.L. and Boyan, B.D., "Ability of Commerical Demineralized Freeze–Dried Bone Allograft to Induce New Bone Formation is Dependent on Donor Age But Not Gender," Journal of Periodontology, vol. 69, No. 4, (Apr. 1998), pp. 470–478.

Rodgers, J.B., Vasconez, H.C., Wells, M.D., DeLuca, P.P., Faugere, M.C., Fink, B.F. and Hamilton, D., "Two Lyophilized Polymer Matrix Recombinant Human Bone Morphogenetic Protein–2 Carriers in Rabbit Calvarial Defects," Journal of Craniofacial Surgery, vol. 9, No. 2, (Mar. 1998), pp. 147–153.

Omura, S., Mizuki, N., Kawabe, R., Ota, S., Kobayashi, S. and Fujita, K., "A Carrier For Clinical Use of Recombinant Human BMP–2: Dehydrothermally Cross–Linked Composite of Fibrillar and Denatured Atelocollagen Sponge," International Journal of Oral and Maxillofacial Surgery, vol. 27, No. 2, (Apr. 1998), pp. 129–134.

von Fraunhofer, J.A., Storey, R.S., Stone, I.K. and Masterson, B.J., "Tensile Strength of Suture Materials," Journal of Biomedical Materials Research, vol. 19, No. 5, (May–Jun. 1985), pp. 595–600.

Damien, C.J. and Parsons, J.R., "Bone Graft and Bone Substitutes: A Review of Current Technology and Applications," Journal of Applied Biomaterials, vol. 2, No. 3, (Fall 1991), pp. 187–208.

Toriumi, D.M., East, C.A., and Larrabee, W.F., "Osteoinductive Biomateiials For Medical Implantation," Journal of Long–Term Effects of Medical Implants, vol. 1, (1991), pp. 53–77.

Paralkar, V.M., Hammonds, R.G. and Reddi, A.H., "Identification and Charachterization of Cellular Binding Proteins (Receptors) For Recombinant Human Bone Morphogenetic Protein 2B, and Initiator of Bone Differentiation Cascade," Proceedings of the National Academy of Sciences of the United States of America, vol. 88, No. 8, (Apr. 15, 1991), pp. 3397–3401.

Metz, S.A., von Fraunhofer, J.A. and Masterson, B.J., "Stress Relaxation of Organic Suture Materials," Biomaterials, vol. 11, No. 3, (Apr. 1990), pp. 197–199.

Wang, E.A., "Bone Morphogenetic Proteins (BMPs): Therapeutic Potential in Healing Bony Defects," Trends in Biotechnology, vol. 11, No. 9, (Sep. 1993), pp. 379–383.

Niederwanger, M. and Urist, M.R., "Demineralized Bone Matrix Supplied by Bone Banks For a Carrier of Recombinant Human Bone Morphogenetic Protein (rhBMP–2): a Substitute For Autogenetic Bone Grafts," Journal of Oral Implantology, vol. 22, Nos. 3–4, (1996), pp. 210–215.

Zellin, G. and Linde, A., "Importance of Delivery Systems For Growth–Stimulatory Factors in Combination With Osteopromotive Membranes. An Experimental Study Using rhBMP–2 in Rat Mandibular Defects," Journal of Biomedical Materials Research, vol. 35, No. 2, (May 1997), pp. 181–190.

Tsuruga, E., Takita, H., Itoh, H., Wakisaka, Y. and Kuboki, Y., "Pore Size of Porous Hydroxyapatite as the Cell–Substratum Controls BMP–Induced Osteogenesis," Journal of Biochemistry, vol. 121, No. 2, (Feb. 1997), pp. 217–324.

Harakas, N.K., "Demineralized Bone–Matrix–Induced Osteogenesis," Clinical Orthopaeidics and Related Research, vol. 188, (Sep. 1984), pp. 239–251.

Johnson, E.E., Urist, M.R., and Finerman, G.A., "Bone Morphogenetic Protein Augmentation Grafting of Resistant Femoral Nonunions. A Preliminary Report," Clinical Orthopaedica and Related Research, vol. 230, (May 1988), pp. 257–265.

* cited by examiner

METHODS AND APPARATUS FOR A COATED ANCHORING DEVICE AND/OR SUTURE

This application is a Continuation-In-Part of and claims priority to U.S. Provisional Application Ser. No. 60/129,675, filed Apr. 16, 1999.

BACKGROUND OF THE INVENTION

1. Technical Field

The present invention generally relates to an anchoring device and/or suture and methods for its use. More particularly, the present invention relates to a coated anchoring device and/or suture and methods for its use.

2. Background Art and Technical Problems

In many surgical procedures requiring tissue to tissue, tissue to bone, and bone to bone fixation, anchoring devices are used in conjunction with a suture to secure the fixation site. For example, the anchoring device could be a screw to join tissue and/or bone, and the suture could be a type of stitch to bind the tissue and/or bone. The anchoring device and/or suture are susceptible to bacteria at every stage of insertion, from external to the body to internal to the tissue and/or bone. Although sterile conditions are desired at each stage of insertion, in practice, that is not always possible. For example, bacteria may originate outside the body and then use the anchoring device and/or suture as a vehicle for invading the body. Alternatively, bacteria may already exist inside the body and the anchoring device and/or suture may carry such bacteria to other areas continuing the infection process.

Sutures are available as both monofilaments and braided filaments with the filaments being comprised of a variety of polymers. The most common suture is a braided polyester. Wicking of bacteria in the suture can be a concern. Braided filaments possess interstices which are sites where bacteria can proliferate. As these bacterial colonies outgrow their homes, they begin to migrate further into the suture causing wicking. Thus, wicking is the process of bacteria infecting the suture and/or surrounding areas.

Sutures may be comprised of a variety of materials including, but not limited to, cellulose (cotton), protein-cellulose (silk), processed collagen (catgut), nylon, polypropylene, Aramid, polyglycolic acid, polyesters, polytetraflourethylene, steel, copper, silver, aluminum, various alloys, Mersilene™, Ticron™, Ethilon™, Prolene™, Ethiflex™, Polyglactin 910™, polyglycolide-lactide polymer (e.g., Vicryl™), polydioxanone (e.g., PDSm™), polyglecaprone 25 (e.g., Monocryl™), polyglyconate (e.g., Maxon™), and Ethibond™.

In other areas of medicine, known methods for reducing the potential for site infection include coatings on catheters or external fixation pins. One common anti-microbial used in these applications is metallic silver. For example, catheters coated with silver have already shown a reduction in infections of the urinary tract where they are used. In addition, antibiotic-impregnated cement has been used for postoperative infections. Fish et al., 49 *Amer Jour Hosp Pharm* 2469 (October 1992). For implant infections, an antibiotic-impregnated silicone rubber coating has been used to cover the implant devices. Rushton et al., 52 *Jour of Neurology, Neurosurgery, and Psychiatry* 223 (1989). Also, recombinant human Transforming Growth Factor-B1 adsorbed onto ceramic implants has been shown to improve bone cell repair. Overgaard et al., 43rd Annual Meeting of the Orthopedic Research Society (San Francisco, Calif., Feb. 9–13, 1997).

However, prior art devices and methods for reducing infection and expediting healing have mainly been directed to implants alone. Such devices and methods have failed to address other key elements introduced into the body during surgery, such as sutures and the problems associated with those elements, such as wicking. Accordingly, a method and apparatus which substantially reduce infection, expedite the healing process, and reduce the problems associated with wicking are needed.

SUMMARY OF THE INVENTION

The present invention includes a coated/impregnated anchoring device and/or suture which prevents infection, delivers site specific drugs, promotes tissue regeneration, and/or promotes bone regeneration in a variety of medical procedures. Coatings for the coated anchoring device and/or suture may include anti-microbial agents for fighting infection, site specific drugs for delivering drugs, or human growth factors for delivering growth factors. Thus, the present invention substantially reduces infection, expedites the healing process, and provides easier drug delivery.

BRIEF DESCRIPTION OF THE DRAWING FIGURES

The subject invention will hereinafter be described in the context of the appended drawing figures, wherein like numerals denote like elements, and:

DETAILED DESCRIPTION

As discussed above, surgical anchoring devices are used in conjunction with surgical sutures to secure the fixation site. Since infection at the operative site and beyond can be a concern, the present invention combines an anti-microbial coating with the anchor and/or suture system commonly used by the surgeon. The present invention adds such a coating to the anchor and/or suture to prevent and reduce infection. The present invention can be used with any implantable surgical device where infection is a potential problem.

Other embodiments disclosed are site specific drug delivery coatings and human growth factor coatings using the existing anchors and/or sutures. For example, anchors and/or sutures comprising certain polymers have the ability to bond to drugs or human growth factors and subsequently release those substances to influence the area into which they are implanted.

Figure 1:
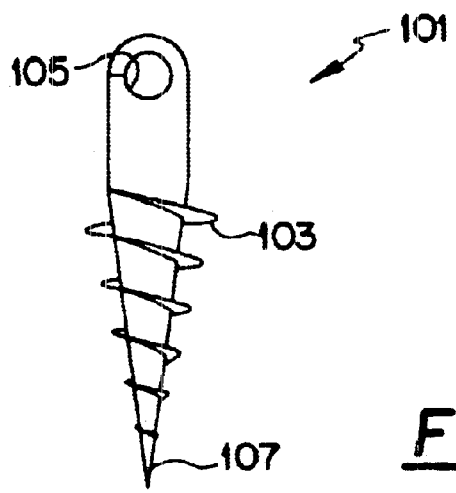
FIG. 1 illustrates a prior art anchoring device.

FIG. 1 illustrates a prior art anchoring device 101 including spiral screw edges 103, a suture hole 105, and a tip 107. As discussed above, anchoring device 101 can be used to attach tissue to tissue, tissue to bone, and/or bone to bone. In addition, anchoring device 101 may be used to attach prosthetic or other materials foreign to the body to tissue and/or bone in the body. The spiral screw edges 103 allow anchoring device 101 to be driven into the tissue and/or bone. In addition, tip 107 provides a sharp edge for the initial insertion or further penetration into the tissue and/or bone. Many metallic and polymeric anchors are available to the surgeon. For example, anchors can be made of any biocompatible material. Examples of biocompatible materials include at least one of stainless steel, titanium, animal bone, cadaveric bone, absorbables, polymers, and the like. Furthermore, examples of polymers include polyester, nylon, poly lactic acid (PLA), poly-L lactic acid (PLLA), poly glycolic acid (PGA), or other bioabsorbable polymer materials.

Figure 2:
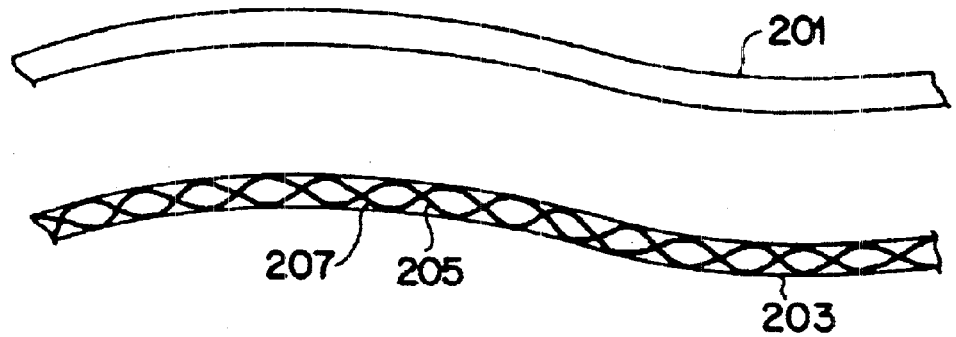
FIG. 2 illustrates a prior art suture and a prior art braided polyester suture.

FIG. 2 illustrates a first prior art suture 201 and a second prior art suture 203. First suture 201 shows a generic suture used to fix tissue and/or bone to tissue and/or bone. First suture 201 loops through anchoring device 01 of FIG. 1 through suture hole 105 to anchor the tissue and/or bone to tissue and/or bone. Likewise, first suture 201 can be used independently to join tissue and/or bone, as is commonly done in stitching.

First suture 201 and second suture 203 can be made of a variety of materials for a variety of uses. For example, second suture 203 is available as a plurality of monofilaments that are braided together where the monofilaments are comprised of a variety of polymers, the most common being braided polyester. The braided interstices 205 and 207 of a braided polyester second suture 203 show where bacteria can proliferate, as discussed above. Thus, wicking of bacteria in the suture can be a concern.

Figure 3:
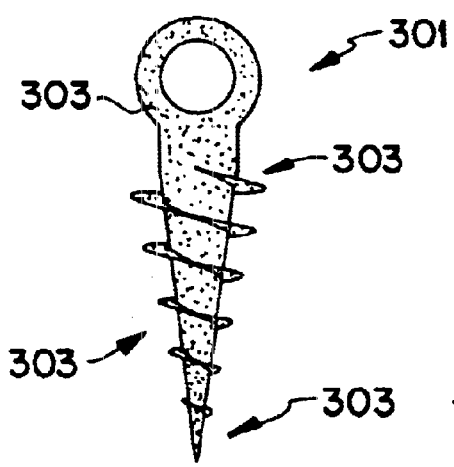
FIG. 3 illustrates a coated anchoring device of the present invention.

FIG. 3 illustrates the present invention embodied in an anchoring device 301. A coating 303 covers anchoring device 301 either partially or completely depending on the desired use. As such, a predetermined portion of anchoring device 301 may be coated depending on the desired use. Additionally, anchoring device 301 may be impregnated by coating 303. Coating 303 can be at least one of an anti-microbial agent, a site specific drug, human growth factors, and the like.

The anti-microbial agents prevent the anchoring device and/or a suture from carrying or transferring infection during insertion of the anchoring device into tissue and/or bone, or at subsequent levels of insertion. The anti-microbial agents create effective barriers to the proliferation of bacteria on or around the anchoring device and/or the suture. In addition, the present invention places effective barriers to the proliferation of bacteria within the suture itself using antimicrobial agents that can be coated, impregnated, and/or bonded to the suture. For example, suitable coatings include at least one of silver, Silicone Rubber Coating, Fibrin Glue, Polymethylmethacrylate (PMMA) Cement, Hydroxyapatite Cement, PMMA Beads, Antibiotic Spray, Biodegradable Collagens, Liposomes, Collagen scaffold, Poylactuc acid microcapsules, Poly-L-lactic Acid (PLLA) scaffold, Polyhydroxyethyl methacrylate (pHEMA), Polyvinylalcohol and gum arabica blend matrix, Xerogel discs using a sol-gel process, and the like. Such suitable coatings may include one or more antimicrobial agents, such as gentamycin, benzethonium chloride, acid antibiotics, penicillin, highheparin content polyquaternary polyurethane elastomers, cephlosporins, penicillanic acids, vancomycin, neomycin, erythromycin, streptomycin, cycloserine, tetracycline, aureomycin, terramycin (oxtetracycline) gentamycin, or polymyxin B, and the like.

Site specific drugs can, for example, enhance tissue or bone regeneration, treat local infection, anesthetize an area, and/or treat a variety of problems. The present invention provides a vehicle for transferring such site specific drugs to the necessary area, such as tissue and/or bone. Alternatively, or in conjunction with the anti-microbial, such site specific drugs may be needed at different levels of insertion of the anchoring device and/or the suture. For example, site specific drugs include at least one of Tobramycin, Gentamicin, Cefazolin, Vancomycin, Cephalothin, Oxacillin-nafcillin, Ceftriaxone, Cefuroxime, Unspecified cephalosporin, Bacitracin, Erythromycin-colistin, Polymyxin B, and the like.

Human growth factors can also enhance tissue and/or bone regeneration or stimulate other desired processes in or around tissue and/or bone. Once again, the present invention provides a vehicle in which such human growth factors can be transferred to the necessary area. Alternatively, or in conjunction with the anti-microbial and/or the site specific drugs, such human growth factors may be needed at different levels of insertion of the anchoring device and/or the suture. For example, anchoring devices made of certain polymers have the capability to bond to drugs or human growth factors and subsequently release the drugs or factors into the necessary area. Examples of such human growth factors include at least one of human growth hormones, morphogenic proteins, Transforming Growth Factor 1, Recombinant Human TGF-1, Bone Morphogenetic Protein-1, Recombinant Human BMP-2, Osteogenic growth peptide, Recombinant Human Growth Hormone, Basic fibroblast Growth Factor, Hepatocyte Growth Factor, and the like.

Coating 303 may be placed on anchoring device 301 and/or a suture (not shown) using a number of different techniques. As discussed above in relation to anchoring device 301, a predetermined portion of the suture may be coated based on the desired use. Any technique that leaves an effective residual on the anchoring device 301 and/or the suture is adequate. For example, possible techniques for applying the suitable coating to anchoring device 301 and/or the suture include at least one of plasma deposition, dipping, wiping, and the like. As long as an effective residual coats the anchoring device and/or the suture, it will be adequate. If the accompanying suture is covered with a metal, then it may be necessary to cover that part of the suture which contacts anchoring device 301 with the suitable coating. Covering the suture with the suitable coating would reduce the potential for galvanic reactions, electrolysis, reactions at the surface, or the like. A separate embodiment would be a suture which is only partially coated.

In addition, anchoring device 301 and/or the suture may be impregnated by coating 303 by any suitable method. For example, anchoring device 301 and/or the suture may be impregnated by coating 303 by compounding, which entraps coating 303 into the biocompatible material that anchoring device 301 and/or the suture are made of. By way of illustration, if anchoring device 301 and the suture are made of a polymer, then mechanical compounding will entrap coating 303 between the interstices of the matrix of the polymer material. Another example of impregnating coating 303 into anchoring device 301 and/or the suture is by chemically bonding coating 303 into the biocompatible material of anchoring device 301 and/or the suture. Thus, mechanically entrapping coating 303 or chemically bonding coating 303 into anchoring device 301 and/or the suture are two examples of methods by which anchoring device 301 and/or the suture may be impregnated by coating 303. Of course, those skilled in the art will appreciate that various other methods of impregnation are available.

Figure 4:
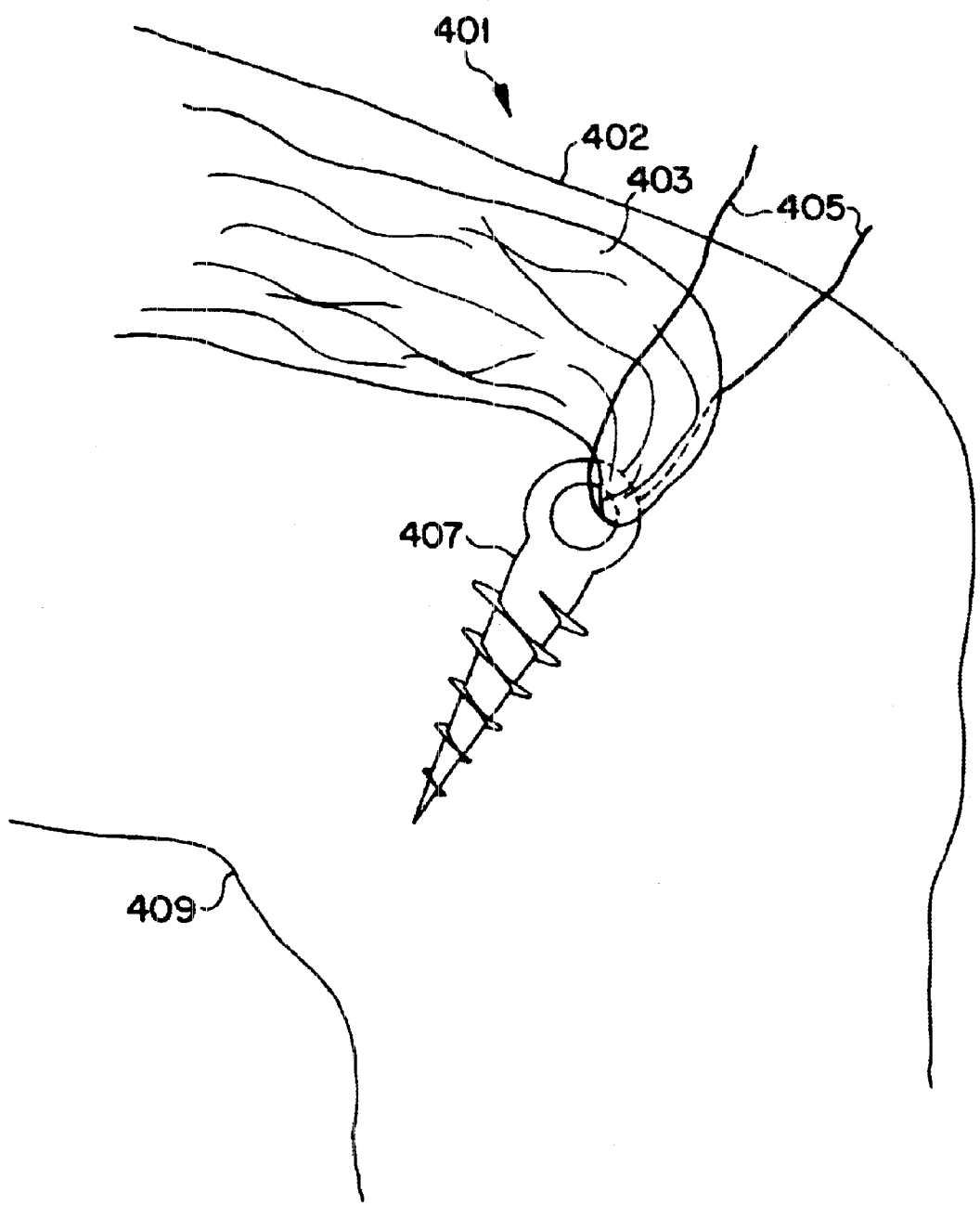
FIG. 4 illustrates an anchoring device and suture of the present invention inserted into a shoulder.

FIG. 4 illustrates how an anchoring device 407 may need to travel through several stages of insertion into a shoulder 401. Shoulder 401 depicts anchoring device 407 with suture 405 traveling through surface tissue 402, muscle and/or ligament 403, and bone 409. At each level of penetration, anchoring device 407 and suture 405 are susceptible to bacteria. A coating on anchoring device 407 and/or suture 405, as discussed above, would prevent such bacteria from proliferating on surface tissue 402, muscle and/or ligament 403, and/or bone 409. Alternatively, or in conjunction with preventing proliferation of bacteria, each level of penetration may require delivery of site specific drugs or human growth factors to the necessary area. The present invention which includes anchoring device 407 and/or suture 405 with a suitable coating could deliver such drugs or factors to the necessary area.

Figure 5:
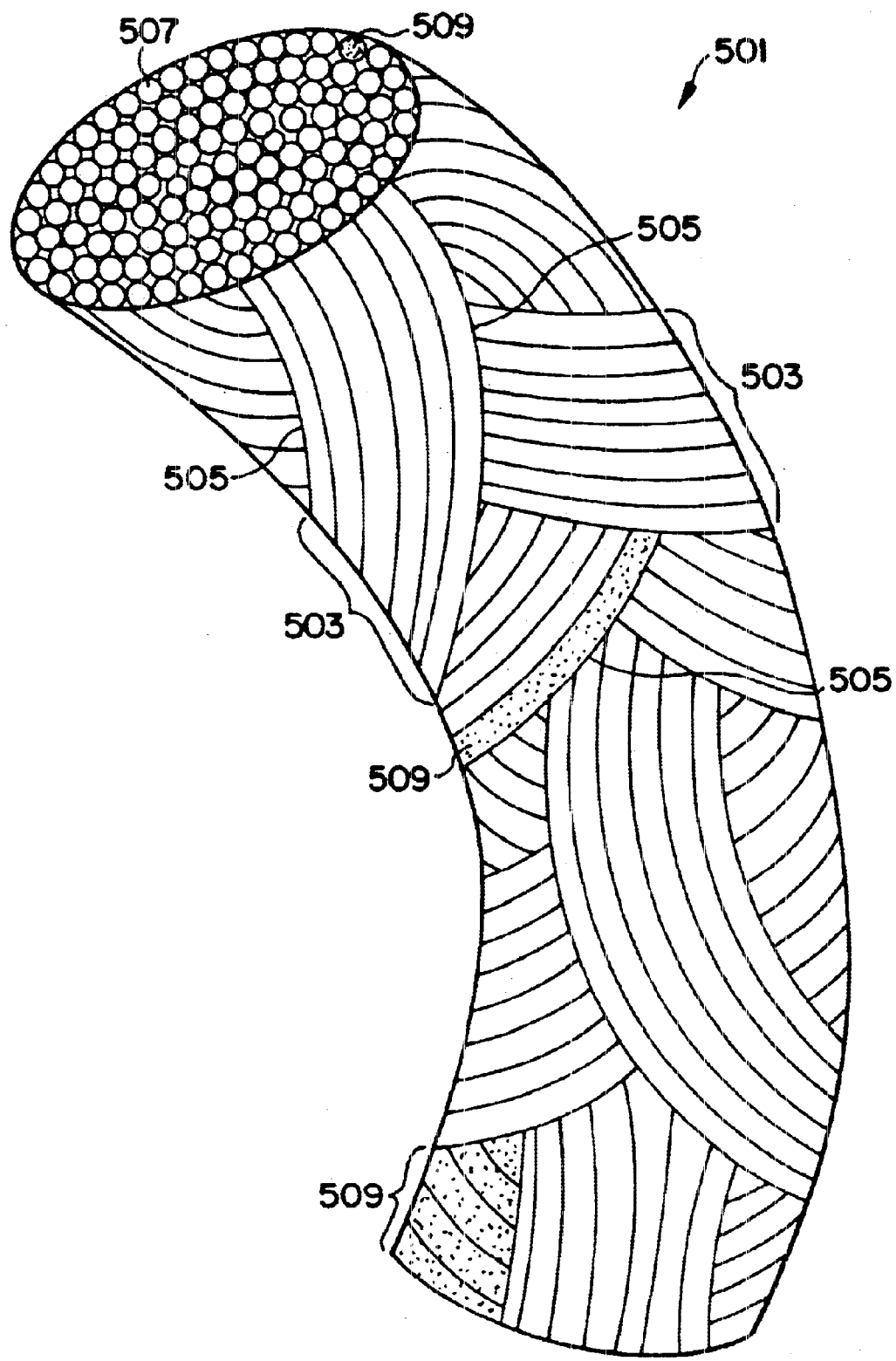
FIG. 5 illustrates a suture of the present invention.

To further illustrate the present invention as applied to a suture 501, refer to FIG. 5. Suture 501 includes a braided section 503, an interstice 505, and an individual fiber 507. In between several braided sections 503, interstices 505 may become infected and cause wicking, as described above. Also, in between individual fibers 507, bacteria and infection can cause wicking. A coating 509, similar to coating 303 of FIG. 3, applied to a predetermined portion of suture 501 may reduce infection, expedite the healing process, and provide easier drug delivery. Coating 509 may be applied to braided section 503, interstice 505, and/or individual fiber 507, and may either partially cover or entirely encapsulate braided section 503, interstice 505, and/or individual fiber 507. In addition, braided section 503, interstice 505, and/or individual fiber 507 may be impregnated with coating 509. Thus, FIG. 5 illustrates one embodiment of the present invention as applied to suture 501.

Figure 6:
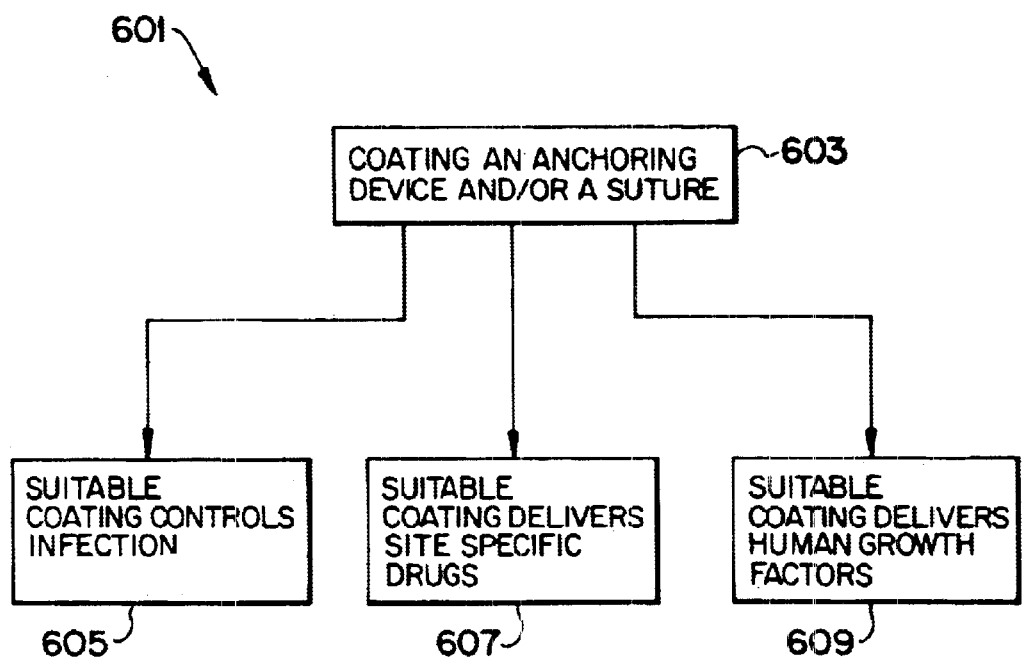
FIG. 6 illustrates a method of coating/impregnating an anchoring device and/or a suture in accordance with the present invention.

Referring now to FIG. 6, flowchart 601 of the present invention illustrates one method of coating/impregnating an anchoring device and/or a suture. In step 603, an anchoring device and/or suture are coated with a suitable coating. Of course, as discussed above, step 603 may alternatively, or also involve impregnating the anchoring device and/or the suture with one or more of an anti-microbial, a site specific drug, or a human growth factor. The suitable coating controls infection in step 605, delivers site specific drugs in step 607, and/or delivers human growth factors in step 609. As discussed above, controlling infection in step 605 may involve using at least one anti-microbial, delivering site specific drugs in step 607 may include at least one of enhancing tissue or bone regeneration, treating local infection, or anesthetizing an area, and delivering human growth factors in step 609 may enhance tissue or bone regeneration, or stimulate other desired processes.

Tissue and/or bone to tissue and/or bone fixation represents one use for the devices and methods embodied in the present invention. Risk of infection is one of the most critical elements in a surgical procedure. Addition of a barrier to infection and prophelactic methods adds an additional level of protection for the patient which can be effective at the implant site and is an improvement over related anchors and/or sutures. In addition, other embodiments of the present invention include coating (and/or impregnating) the anchoring device and/or suture with site specific drugs and/or human growth factors to promote tissue regeneration, bone regeneration, or other desired bodily processes.

Although the invention has been described herein with reference to the appended drawing figures, it will be appreciated that the scope of the invention is not so limited. Various modifications in the design and implementation of various components and method steps discussed herein may be made without departing from the spirit and scope of the invention, as set forth in the appended claims.

What is claimed is:

1. A medical device comprising:

a suture anchor; and a coating covering a predetermined portion of said suture anchor, wherein said coating includes at least one of an anti-microbial agent or a site specific drug, wherein said coating includes at least one of:

a silver, a Silicone Rubber Coating, a Fibrin Glue, a Polymethylethacrylate (PMMA) Cement, a Hydroxyanatite Cement, a plurality of PMMA Beads, an Antibiotic Spray, a biodegradable Collagen, a Liposomes, a Collegen Scaffold, a Poylactuc acid microcapsule, a Poly-L-lactic Acid (PLLA) scoffold, a Polyhydroxyethyl methacrylate (pHEMA), a Polwvinylalcholo and a gum arabica blend matrix, or a plurality of Xerogel discs using a solgel process; and a gentamycin, a benzethonium chloride, an acid antibiotic, a penicillin, a high heparin content polyquaternary polyurethane elastomer, a cephiosporin, a penicillanic acid, a vancomycin, a neomycin, an erythromycin, a streptomycin, a cycloserine, a tetracycline, an aureomycin, a terramycin (oxtetracycline) gentamycin, or a polymyxin B.

2. The device of claim 1 wherein said suture anchor comprises a biocompatible material.

3. The device of claim 2 wherein said biocompatible material includes at least one of a stainless steel, a titanium, a polymer, a bone, or an absorbable.

4. The device of claim 3 wherein said polymer includes at least one of a polyester, a nylon, a poly lactic acid (PLA), a poly-L lactic acid (PLLA), or a poly glycolic acid (PGA).

5. The device of claim 1 further comprising a surgical suture.

6. The device of claim 5 wherein said surgical suture comprises a biocompatible material including at least one of a polymer, a cellulose based (cotton), a protein-cellulose (silk), a processed collagen (catgut), a nylon, a polypropylene, an Aramid, a polyglycolic acid, a polyesters, a polytetraflourethylene, a steel, a copper, a silver, an aluminum, an alloy, a polyglycolide-lactide polymer, a polydioxanone, a polyglecaprone 25, or a polyglyconate.

7. The device of claim 5 wherein a predetermined portion of said surgical suture is coated with at least one of a bactericide, a site specific drug, or a human growth factor.

8. The device of claim 7 wherein said human growth factor includes at least one of a human growth hormone, a morphogenic protein, a Transforming Growth Factor 1, a Recombinant Human TGF-1, a Bone Morphogenetic Protein-1, a Recombinant Human BMP-2, an Osteogenic growth peptide, a Recombinant Human Growth Hormone, a Basic fibroblast Growth Factor, or a Hepatocyte Growth Factor.

9. The device of claim 7 wherein said human growth factor includes at least one of a human growth hormone, a morphogenic protein, a Transforming Growth Factor 1 a Recombinant Human TGF-1, a Bone Morphogenetic Protein-1, a Recombinant Human BMP-2, an Osteogenic growth peptide, a Recombinant Human Growth Hormone, a Basic fibroblast Growth Factor, or a Hepatocyte Growth Factor.

10. The device of claim 5 wherein said surgical suture is impregnated with at least one of an anti-microbial, a site specific drug, or a human growth factor.

11. The device of claim 5 wherein said surgical suture comprises a biocompatible material and is coated with said coating.

12. The device of claim 5 wherein said site specific drug includes at least one of a Tobramycin, a Gentamicin, Cefazolin, a Vancomycin, a Cephalothin, an Oxacillin-nafoillin, a Ceftriaxone, Cefuroxime, an Unspecified cephalosporin, a Bacitracin, an Erythromycin-colistin, or Polymyxin B.

13. The device of claim 12 wherein said coating is impregnated into at least one of said suture anchor or said surgical suture.

14. The device of claim 5 wherein said anti-microbial agent includes a gentamycin, a benzethonium chloride, an acid antibiotic, a penicillin, a high-heparin content polyquaternary polyurethane elastomer, a cephlosporin, a penicillanic acid, a vancomycin, a neomycin, an erythromycin, a streptomycin, a cycloserine, a tetracycline, an aureomycin, a terramycin (oxtetracycline) gentamycin, and a polymyxin B.

15. The device of claim 14 wherein said coating is impregnated into at least one of said suture anchor or said surgical suture.

16. The device of claim 1 wherein said site specific drug includes at least one of a Tobramycin, a Gentamicin, Cefazolin, a Vancomycin, a Cephalothin, an Oxacillinnafcillin, a Ceftriaxone, a Cefuroxime, an Unspecified cephalosporin, a Bacitracin, an Erythromycin-colistin, or a Polymyxin B.

17. The device of claim 1 wherein the coating is impregnated into the suture anchor.

18. A method for coating a suture anchor comprising the steps of:

coating said suture anchor with a suitable coating; and configuring said suitable coating to include at least one of controlling infection or delivering site specific drugs, wherein said suitable coating comprises at least one of:

a silver, a Silicone Rubber Coating, a Fibrin Glue, a Polymethylmethacrylate (PMMA) Cement, a Hydroxyapatite Cement, a plurality of PMMA Beads, an Antibiotic Spray, a Biodegradable Collagen, a Liposomes, a Collagen scaffold, a Poylactuc acid microcansule, a Poly-L-lactic Acid (PLLA) scaffold, a Polyhydroxyethyl methacrylate (pHEMA), a Polyvinylalcohol and a gum arabica blend matrix, or a plurality of Xerogel discs using a sol-gel process; and a gentamycin, a benzethonium chloride, an acid antibiotic, a penicillin, a high-heparin content polyvuaternary polyurethane elastomer, a cephlosporin, a penicillanic acid, a vancomycin, a neomycin, an erytbromycin, a streptomycin, a cycloserine, a tetracycline, an aureomycin, a terramycin (oxtetracycline) gentamycin, or polymyxin B.

19. The method of claim 18 further comprising the step of coating a suture with said suitable coating.

20. The method of claim 19 wherein said suture comprises a biocompatible material including at least one of a polymer, a cellulose based (cotton), a protein-cellulose (silk), a processed collagen (catgut), a nylon, a polypropylene, an Aramid, a polyglycolic acid, a polyesters, a polytetraflourethylene, a steel, a copper, a silver, an aluminum, an alloy, a polyglycolide-lactide polymer, a polydioxanone, a polyglecaprone 25, or a polyglyconate.

21. The method of claim 19, wherein said suture comprises braided filaments having interstices and said suitable coating covers a predetermined portion of said interstices of said suture.

22. The method of claim 21 further comprising impregnating said suitable coating into said suture.

23. The method of claim 19 further comprising impregnating said suitable coating into at least one of said suture anchor or said suture.

24. The method of claim 19 wherein said suitable coating comprises a human growth factor including a human growth hormone, a morphogenic protein, a Transforming Growth Factor 1, a Recombinant Human TGF-1, a Bone Morphogenetic Protein-1, a Recombinant Human BMP-2, an Osteogenic growth peptide, a Recombinant Human Growth Hormone, a Basic fibroblast Growth Factor, or a Hepatocyte Growth Factor.

25. The method of claim 18 wherein said suture anchor comprises a biocompatible material wherein said biocompatible material includes at least one of a stainless steel, a titanium, a polymer, a bone, or an absorbable.

26. The method of claim 25 wherein said polymer includes at least one of a polyester, a nylon, a poly lactic acid (PLA), a poly-L lactic acid (PLLA), or a poly galactic acid (PGA).

27. The method of claim 18 wherein said suitable coating comprises at least one site specific drug including a Tobramycin, a Gentamicin, a Cefazolin, a Vancomycin, a Cephalothin, an Oxacillin-nafcillin, a Ceftriaxone, a Cefuroxime, an Unspecified cephalosporin, a Bacitracin, an Erythromycin-colistin, or a Polymyxin B.

28. The method of claim 18 wherein:

said suture comprises braided filaments having interstices and said suitable coating covers a predetermined portion of said interstices of said suture.

29. The method of claim 28 further comprising impregnating said suitable coating into at least one of said suture anchor or said suture.

30. The method of claim 18 wherein coating the suture anchor includes impregnating the suitable coating into the suture anchor.

* * * * *